US005849987A

United States Patent [19]
Reisner

[11] Patent Number: 5,849,987
[45] Date of Patent: Dec. 15, 1998

[54] ANIMAL MODEL FOR HEPATITIS VIRUS INFECTION

[75] Inventor: Yair Reisner, Tel Aviv, Israel

[73] Assignee: Yeda Research and Development Co. Ltd., Rehovot, Israel

[21] Appl. No.: 242,580

[22] Filed: May 13, 1994

Related U.S. Application Data

[63] Continuation-in-part of Ser. No. 61,706, May 17, 1993, which is a continuation-in-part of Ser. No. 892,911, Jun. 2, 1992, abandoned.

[30] Foreign Application Priority Data

Sep. 8, 1993 [IL] Israel ................................... 106951

[51] Int. Cl.⁶ .............................. C12N 5/06; C12N 15/09
[52] U.S. Cl. ................................... 800/2; 435/172.3
[58] Field of Search ............................... 800/2; 424/93.2, 424/93.21, 7; 435/172.3; 514/44

[56] References Cited

U.S. PATENT DOCUMENTS

| 4,683,200 | 7/1987 | Hirohashi et al. ............... 435/70.21 |
| 5,147,784 | 9/1992 | Peault ............................ 435/7.24 |

FOREIGN PATENT DOCUMENTS

| 0 322 240 | 6/1989 | European Pat. Off. . |
| 0438053 | 7/1991 | European Pat. Off. . |
| 0469632 | 2/1992 | European Pat. Off. . |
| 0517199 | 12/1992 | European Pat. Off. . |
| 89/12823 | 12/1989 | WIPO . |
| 91/16451 | 10/1991 | WIPO . |
| 91/16910 | 11/1991 | WIPO . |
| 91/18615 | 12/1991 | WIPO . |
| 92/03918 | 3/1992 | WIPO . |
| 92/06715 | 4/1992 | WIPO . |

OTHER PUBLICATIONS

Barry, et al, "Successful Engraftment of Human Postnatal Thymus in Severe Immune Deficient (SCID) Mice: Differential Engrafment of Thymic Components with Irradiation Versus Anti–asialo GM–1 Immuno–Suppressive Regimens", *J. Exp. Med.*, 173:167–180 (1991).

Bosma, et al, "A Severe Combined Immunodeficiency Mutation in the Mouse", *Nature* 301:527–531 (1983).

Giovanella, et al, "Heterotransplantation of Human Cancers into Nude Mice", *Cancer,* 42:2269–2281 (1978).

Kamel–Reid, et al, "Engraftment of Immune–Deficient Mice with Human Hematopoietic Stem Cells", *Science,* 242:1706–1708 (1988).

Kamel–Reid, et al, "A Model Human Acute Lymphoblastic Leukemia in Immune–Deficient SCID Mice", *Science,* 246:1597–1600 (1989).

Keever, et al, "Immune Reconstitution Following Bone Marrow Transplantation: Comparison of Recipients of T–Cell Depleted Marrow WIth Recipients of Conventional Marrow Grafts", *Blood,* 73:1340 (1989).

McCune, et al, "The SCID–hu Mouse: Murine Model for hte Analysis of Human Hematolymphoid Differentiation and Function", *Science,* 241:1632–1639 (1988).

McCune, et al, "Pseudotypes in HIV–Infected Mice", *Science,* 250:1152–1154 (1990).

Miyami–Inaba, et al, "Isolation of Murine Pluripotent Hematopoietic Stem Cells in the Go Phase", *Biochemical and Biophysical Research Communications,* 147(2):687–695 (1987).

Mosier et al, "Transfer of a Functional Human Immune System to Mice with Severe Combined Immunodeficiency", *Nature,* 225:256–259 (1988).

Murphy, et al, "An Absence of T Cells in Murine Bone Marrow Allografts Leads to an Increased Susceptibility to Rejection by Natural Killer Cells and T Cells", *Journal of Immunology,* 144:3305–3311 (1990).

Namikawa, et al, "Infection of the SCID–hu Mouse by HIV–1", *Science,* 242:1684–1686 (1988).

Reisner, et al, "Transplantation for Severe Combined Immunodeficiency with HLA–A, B, D, DR Incompatible Parental Marrow Cells Fractioned by Soybean Agglutinin and Sheep Red Blood Cells", *Blood,* 61:341 (1983).

Schuler, et al, "Rearrangement of Antigen Receptor Genese in Defective Mice with Severe Combined Immune Deficiency", *Cell* 46:963–972 (1986).

*Stedman's Medical Dictionary,* 24th ed., Williams & Wilkins, Baltimore, 1982, p. 1242.

Sykes, et al, "Mixed Allogeneic Chimerism as an Approach to Transplantation Tolerance", *Immunology Today,* 9(1):23–27 (1988).

van Bekkum, et al, "Immune Reconstitution of Radiation Chimeras", *Bone Marrow Transplantation: Biological Mechnisms and Clinical Practice,* Dekker, New York, pp. 311–350.

Nakakawa et al. Oct. 1990. J. Exp. Med. 172:1055–1063.

Galun, E., et al., "Hepatitis C Viremia In Chimeric Mice", *Hepatology,* vol. 20, No. 4/2, p. 232A, Oct. 1994, 45th Annual Meeting of the American Association for the Study of Liver Diseases, Nov. 11–15, 1994.

(List continued on next page.)

*Primary Examiner*—Brian R. Stanton
*Attorney, Agent, or Firm*—Browdy and Neimark

[57] ABSTRACT

Chimeric mouse and rat models useful as models for human hepatitis virus (HV) infection are disclosed. These chimeras are made by substantially destroying the hematopoietic cells of a host mouse or rat and then transplanting into the resultant animal hematopoietic cells from SCID mice. The resultant chimera is then used as a host for transplantation of xenogeneic liver tissue, including liver tissue from humans. The liver tissue may be infected with HV either prior to or after transplantation.

12 Claims, 6 Drawing Sheets

OTHER PUBLICATIONS

Lubin, I., et al., "Engraftment and Development of Human T and B Cells in Mice After Bone Marrow Transplantation", *Science*, vol. 252, pp. 427–431, 19 Apr. 1991.

Lubin, I., et al., "Engraftment of Human Peripheral Blood Lymphocytes in Normal Strains of Mice", *Blood*, vol. 83, No. 8, pp. 2368–2381, 15 Apr. 1994.

Mosierm D.E., "Adoptive Transfer of Human Lymphoid Cells to Severely Immunodeficient Mice: Models for Normal Human Immune Function, Autoimmunity, Lymphomagenesis, and AIDS", *Advances in Immunology*, vol. 50, pp. 303–325, 1991.

Nakamura, T., et al., "Successful Liver Allografts in Mice by Combination with Allogeneic Bone Marrow Transplantation", *PNAS*, vol. 83, pp. 4529–4532, Jun. 1986.

Shimizu, Y.K., et al., "Correlation Between the Infectivity of Hepatitis C Virus In Vivo and Its Infectivity In Vitro", *PNAS*, vol. 90, pp. 6037–6041, Jul. 1993.

ANIMAL MODEL FOR HEPATITIS VIRUS INFECTION

CROSS-REFERENCE TO RELATED APPLICATIONS

The present application is a continuation-in-part of copending application Ser. No. 08/061,706, filed May 17, 1993, which is a continuation-in-part of application Ser. No. 07/892,911, filed Jun. 2, 1992, now abandoned.

FIELD OF INVENTION

The present invention concerns an animal model for hepatitis virus (HV) infection in humans, particularly hepatitis B virus (HBV) and hepatitis C virus (HCV) infection.

PRIOR ART

The following is a list of prior art and references considered to be pertinent for the description below:

1. Choo, Q-L, Kuo G, Weiner, A. J. Overby L. R., Bradley D. W., Houghton, M. Isolation of CDNA clone derived from a blood-borne non-A, non-B viral hepatitis genome. 1989. *Science* 244:359–362.
2. Kuo G, Choo Q-L, Alter H. J., Gitnick, G. L., Redeker A. G., Purcell R. H., Miyamura T, Dienstag J. L., Alter H. J. Stevenes C. E., Tegtmeier G. E., Bonnino F., Colombo M. Lee W-S, Kuo C, Berger K, Shuster J. R., Overby L. R., Bradley D. W., Houghton M. 1989. An essay for circulating antibodies to major etiologic virus of human non-A, non-B hepatitis. *Science* 244:362–344.
3. Prince, A. M., Brotman B., Huima T., Pascual D., Jaffery M. Inchauspe G. 1992. Immunity in hepatitis C infection. *J. Infec. Dis.* 165:438–443.
4. Shimizu Y. K., Weiner, J. Rosenblatt J., Wong D. C., Shapiro M., Popkin T, Houghton M, Alter H. J., Purcell R. H. 1990. Early events in hepatitis C virus infection in chimpanzees. *Proc. Natl. Acad. Sci.* (USA) 87:6441–6444.
5. Shimizu, Y. K., Iwamoto A., Hijikata M., Purcell R. H., Yoshikura H. 1992. Evidence for in vitro replication of hepatitis C virus genome in a human T cell line. *Proc. Natl. Acad. Sci.* (USA) 89:5477–5481.
6. Shimizu Y. K., Purcell R. H., Yoshikura H. 1993. Correlation between the infectivity of hepatitis C virus in vivo and its infectivity in vitro. *Proc. Natl. Acad. Sci.* (USA) 90:6037–6041.
7. Nakamura T., Good R.A., Yasumizu R., Inoue S., Oo M. M., Hamashima Y, Ikehara S. 1986. Successful liver allografts in mice by combination with allogeneic bone marrow transplantation. *Proc. Natl. Acad. Sci.* (USA) 83:4529–45326.
8. Bosma, M. J. Carroll, A. M. 1991. The SCID mouse mutant: Definition, characterization, and potential uses. *Annu. Rev. Immunol.* 9:323–350.
9. Soriano, H. E., Adams, R. M., Darlington G., Finegold M. Steffen D. L., Ledley F. D. 1992. Retroviral transduction of human hepatocytes and orthotopic engraftment in SCID mice after hepatocellular transplantation. *Trans. Proc.* 24:3020–3021.
10. Aldrovandi G. M., Feurer G., Gao L., Jamieson B., Kristeva M., Chen I. S. Y., Zack J. A., 1993. The SCID-hu mouse as a model for HIV-1 infection. *Nature* 363:732–736.
11. European laid open Patent Application, Publication No. 438053.
12. European laid open Patent Application, Publication No. 517199.

The citation herein of the above publications is given to allow an appreciation of the prior art. This citation should not, however, be construed as an indication that this art is in any way relevant to the patentability of the invention, as defined in the appended claims.

The above publications will be acknowledged herein by indicating their number from the above list.

BACKGROUND OF THE INVENTION

Five different viruses have been identified as causes of viral hepatitis. These include hepatitis A, B, C, D and E viruses. Of these, the viruses which cause the most serious infections are hepatitis B virus (HBV) and hepatitis C virus (HCV).

Hepatitis A virus has a single serotype and causes a self-limited acute infection. A large percentage of the population, approaching 50%, has hepatitis A antibodies in serum and is probably immune to disease. Infection with hepatitis A does not progress to chronic disease.

HBV is implicated in both acute and chronic hepatitis. The disease is endemic in Asia, is increasing in prevalence in the U.S. and Europe. Chronic liver disease, resulting in significant morbidity and increased mortality, is sequela of infection in 1–10% of infected individuals. HBV infection is also correlated with the development of primary liver cancer.

HCV was recently shown to be the major causative agent of parenterally transmitted non-A, non-B hepatitis[1]. It is estimated that 0.5–1% of the world population is infected with HCV, and in some developing countries the prevalence rate is up to 40%. Moreover, 40–60% of newly infected patients develop persistent HCV infections[2] and are at risk of developing acute, fulminant hepatitis and various chronic liver diseases (including cirrhosis, chronic active hepatitis and in some cases hepatocellular carcinoma).

Hepatitis D virus ("Delta Virus") is a defective RNA virus that can only infect the liver in the presence of an active HBV infection. Hepatitis E virus appears to be a single-stranded RNA virus. Infection with hepatitis E virus is not known to progress to chronic liver disease.

Although HBV and HCV have been identified and characterized, the development of new anti-viral strategies has been greatly hampered by the lack of adequate, simple and low cost animal model systems.

Currently, biological assays for HBV and HCV have been limited to the experimental inoculation of chimpanzees[3,4], which are expensive and limited in numbers. In addition, an in vitro system for the propagation of HCV was developed in the murine retrovirus infected human T cell lines, HPB-Ma[5] and Molt4-Ma[6], in which replication of HCV is achieved.

It has recently been demonstrated in several studies that human solid organs such as fetal thymus or fetal liver as well as several types of tumors were successfully grafted into SCID mice under the kidney capsule[7]. In addition, transplantation of other organs such as lymph nodes and bone marrow spicules and engraftment of organs to other sites (i.e. subcutane and peritoneum) have also been reported.

A SCID mouse mutant was reported to support human cell implantation, i.e. single hepatocyte transplantation[8,9], and was also used as a model for human infectious diseases, i.e. HIV-1 infection[10].

It has been disclosed that lethally irradiated mice, radio-protected with bone marrow from SCID mice, developed marked immune-deficiency and supported engraftment of human peripheral blood lymphocytes (PBL) for a long period of time$^{(11)}$. It was also disclosed that human implants of non-hematopoietic origin were accepted and maintained for prolonged periods of time after transplantation under the kidney capsules of these chimeras$^{(12)}$.

GENERAL DESCRIPTION OF THE INVENTION

It is an object of the present invention to provide a convenient non-human animal model for HV infection.

It is further an object of the present invention to provide a method for evaluation of preventive and therapeutic agents for the treatment and prophylaxis of HV infections using the above non-human animal model.

It is still another object of the present invention to provide methods for production of anti-HV xenogeneic antibodies or T cells, and particularly human monoclonal antibodies and cytotoxic T cells, using chimeric non-human mammals transplanted with human hematopoietic cells and human liver tissue infected by HV either pre- or post-transplant.

The present invention provides, by its first aspect, a non-human chimeric animal useful as a model for human HV infection, comprising a mammal M5 having xenogeneic cells; mammal M5 being derived from a mammal M1 treated to substantially destroy its hematopoietic cells and then transplanted with hematopoietic cells derived from one or more mammals M2 and transplanted with liver tissue from a mammal M3, the one or more mammals M2 and mammal M3 being from the same or from a different species; the transplanted hematopoietic cells from the one or more mammals M2 being either one or both of a hematopoietic cell preparation from a T cell deficient mammal or of a T cell depleted mammalian stem cell or bone marrow preparation; the transplanted liver tissue from mammal M3 being either a human liver tissue preparation or a liver tissue preparation from a non-human mammal capable of being infected by HV; the liver tissue preparation in the M5 mammal being infected by HV.

The M1 mammal may typically be a mouse or a rat, although the M1 mammal may also be a non-human mammal of a higher order such as a primate, e.g. marmoset monkeys.

For the obtaining of an M5 mammal from said M1 mammal, the M1 mammal is first treated in a manner so as to substantially destroy its hematopoietic system. The term "substantially destroyed" should be understood as meaning that the number of hematopoetic cells which survive following the treatment are insufficient to immune-protect the animal in the absence of the transplant from the M2 mammal. Following treatment intended to substantially destroy the hematopoietic cells, some such cells survive but the number is small such that the animal could not survive under normal laboratory conditions.

A treatment intended to substantially destroy the hematopoietic cells may, for example, be a split dose total body irradiation, (TBI). A TBI effective in destroying the hematopoietic system requires typically an accumulative dosage of 4–50 Gy (1 Gy=100 rad). In the case of a mouse, the irradiation may, for example, be a 4 Gy on day 1 and 9–15 Gy three days later. A similar irradiation dose was found to be effective in destroying the hematopoietic cells also in rats and marmoset monkeys.

The M2 mammal may be from the same or a different species than the M1 mammal. In principle, any mammal with a T cell deficiency may serve as a donor for the transplanted hematopoietic cells. An example of an M2 donor is a severe combined immuno-deficient (SCID) mouse or a SCID animal from another mammalian species or genera. The transplanted hematopoietic cell preparation in this case is suitably a bone marrow preparation.

The transplanted hematopoietic cells derived from the M2 mammal may also be a T cell depleted hematopoietic stem cell preparation obtained from a donor M2 mammal, such as a primate, e.g. a monkey or a human. In the case of humans, a stem cell enriched preparation may, for example, be obtained from peripheral blood of donors pretreated with a granulocyte colony stimulating factor (G-CSF) or from cancer patients undergoing chemotherapy known to cause migration of stem cells to the periphery. After withdrawal of the blood preparation from such donors, the preparation is typically treated to remove various blood components and to deplete the T cells therefrom. For T cell depletion, the M2 derived D hematopoietic cell preparation may be subjected to treatment intended for enrichment with cells displaying the CD34 antigen (CD34$^+$ cells). Each of the above stem cell enriched, T cell depleted preparations can either be used directly after their withdrawal from the donor, or may be a cell-preparation which underwent one or a plurality of passages in vitro.

The transplanted hematopoietic cells may also be a T cell depleted bone marrow preparation.

The M1 mammal may also be transplanted with both a hematopoietic cell preparation from a T cell deficient mammal and a T cell depleted mammalian stem preparation. A specific example is a combined transplantation of bone marrow from a SCID mammal, e.g. a SCID mouse, and a T cell depleted human bone marrow preparation.

In order to obtain the M5 mammal, the M1 mammal may be transplanted with an HV infected liver tissue. Such an HV infected liver tissue may be obtained from an M3 mammal infected with HV, e.g. a liver biopsy from an HV infected human. Furthermore, an HV infected liver tissue preparation may also be obtained by in vitro infection of an a priori non-HV infected liver tissue preparation obtained from a non-HV infected M3 donor mammal. Alternatively, rather than transplanting the M1 mammal with an HV infected liver tissue, the M1 mammal may first be transplanted with liver tissue not infected by HV, thus obtaining an M4 mammal, and then inoculating the M4 mammal with HV leading to infection of the transplanted liver tissue.

An M4 mammal may thus serve as a model for testing the efficacy of an agent in the prophylaxis of HV. In such a model, the putative prophylactic agent is administered to the M4 mammal either prior or together with the HV and its ability to inhibit HV infection can then be determined.

In addition to human liver tissue preparation, it is also possible to use liver tissue preparations from non-human M3 mammals susceptible to HV infections such as chimpanzees or other non-human primates.

The animal model of the invention is particularly suitable for the study of the pathology for HBV and HCV infections and the development of therapies therefor. Models for both HBV and HCV are particularly preferred in accordance with the invention, as no simple and low cost models for these viral infections are currently available.

The invention further provides, by a second of its aspects, a method for evaluating the potential of an agent or a combination of agents in the therapy of an HV infection, comprising:

(a) obtaining an M5 mammal as defined above;

(b) administering said agent or said combination of agents to said M5 mammal; and (c) evaluating the effectiveness of said agent or said combination of agents in preventing spread of HV infection, reducing its physiological symptoms or reducing the evidence of active infection in said M5 mammal.

The present invention still further provides, by a third of its aspects, a method for evaluating the potential of an agent or a combination 5 of agents, in the prevention of an HV infection, comprising:

(a) obtaining said mammal M4;

(b) administering said agent or said combination of agents to said M4 mammal;

(c) infecting said M4 mammal with HV; and (d) evaluating the effectiveness of said agent or said combination of agents in preventing primary HV infection of the liver tissue of said M4 mammal.

By a modification thereof, the methods according to the second or third aspects, may also be applied in determining the effective dose of said agent or said combination of agents in therapy or prevention, as the case may be.

By a fourth of its aspects, the present invention provides a method of obtaining anti-HV immune cells or antibodies, comprising:

(a) obtaining a mammal M5, as defined above, wherein at least one of said one or more M2 mammals is human;

(b) recovering immune cells or antibodies from the blood of said M5 mammal; and (c) selecting for the immune cells or antibodies having an anti-HV reactivity.

Optionally, in accordance with the fourth aspect, the M5 mammal, is treated so as to increase the immune response against HV, such as for example by vaccination.

The selected immune cells may be cytotoxic T cells reactive against HV infected liver cells. Such a cytotoxic T cell preparation may be obtained by growing lines of T cells obtained from the M5 mammal and then selecting those lines which develop a cytotoxic cell response against cells expressing HV antigens. Such a cytotoxic T cell preparation may be injected to HV patients within the framework of an anti-HV therapy.

The selected immune cells may also be antibody producing B cells immortalized and selected for those producing anti-HV antibodies. The antibodies produced by these B cells may then be used as therapeutic agents in anti-HV therapies of hepatitis patients.

The manner of growing cytotoxic T cell lines, the manner of immortalization of B cells to produce B cell lines, as well as the manner of selecting specific cytotoxic T cells or immortalized B cell lines to obtain those having the desired reactivity, is generally known per se and the full explanation of such methods goes beyond the present writing.

The invention will now be described with reference to some specific embodiments described in the following examples and the appended drawings.

DESCRIPTION OF THE DRAWINGS

FIG. 4A, are from mice at day 9 after transplantation. The remaining lanes are from days 14–53 after transplantation (the days are indicated above the lanes). The last two lanes are negative control (−) and positive control (+).

EXAMPLES

Figure 1A:
FIGS. 1A –1C show histology of liver tissue transplanted under the kidney capsule of SCID→BNX chimera, 1 month after transplantation of liver fragments from BNX mouse (A), Lewis rat (B), or human (C). All transplanted animals which survived the kidney subcapsular implantation of liver tissue were assessed for engraftment by light microscopy of the kidneys using H&E staining.

Example 1
Engraftment of Human Liver Segment from non-HCV Patients

BNX mice (6–10 weeks old, female) were purchased from Harlam Sprague-Dawley (Indianapolis, Ind.) and CB17/ SCID mice were from the Animal Breeding Center. Weizmann Institute, Rehovot, Israel. Mice were kept in small cages (5 animals in each cage) and fed sterile food and acid water containing cyprofloxacin (20 mg/ml). Prior to transplantation, the BNX mice were conditioned with 12 Gy TBI and radioprotected the following day with $2-3 \times 10^6$ T cell depleted SCID bone marrow cells. TBI was administered from a gamma beam 150-A $^{60}$Co source (Atomic Energy of Canada, Kanata, Ontario) with F.S.D. of 75 cm and a dose rate of 0.7 Cy/min. Bone marrow cells obtained from SCID mice (4–10 weeks old) were fractionated by differential agglutination with soybean agglutinin (to remove T lymphocytes that may be present in occasional "leaky" SCID mice) as previously described[11]. One day after bone marrow transplantation, human, rat or mouse liver fragments were grafted under the kidney capsule.

Rat and mouse liver tissue fragments were collected through laparotomy, in which a wedge biopsy was cut from the animal liver and kept under sterile conditions at 4° C., in Dulbecco modified Eagle medium containing 10% fetal calf serum or ViaSpan (Belzer UW solution, Du Pont Pharmaceuticals, Hertogenbosch, The Netherlands).

Human liver segments were obtained during hepatic segmentectomy when performed for primary or secondary liver tumors. In all cases, the non-tumor tissue was non-cirrhotic, as confirmed by hematoxylin and eosin (H&E) staining. The liver segments were kept, for up to 2 hours in UW solution prior to transplantation. For engraftment of liver tissue, BNX mice were anesthetized with Nembutol or Avertin. An incision of approx. 1 cm was then made in the right or left flank, the kidney was exposed and liver tissue (cut into 1 mm$^2$ pieces) was placed under the renal capsule using fine forceps. One suture was placed to close the wound. Kidneys, with the attached transplanted tissue, were removed at various time intervals (from 8 days to 3 months), fixed in Bouin's liquid, embedded in paraffin, and 4 μm sections were stained with H&E.

A summary of the transplantations of liver fragments in the SCID→BNX chimeric mice is shown in the following Table 1.

TABLE 1

| Number of Mice | | | | Follow-up |
|---|---|---|---|---|
| Transplanted | Surviving | Engrafted | Source of liver | (weeks) |
| 10 | 9 | 4 | Mouse | 10 |
| 20 | 12 | 8 | Mouse | 3 |
| 10 | 7 | 4 | Mouse | 1.4 |
| 10 | 10 | 8 | Rat | 10 |
| 20 | 8 | 5 | Rat | 8 |
| 20 | 7 | 2 | Rat | 2 |
| 10 | 5 | 2 | Rat | 1.4 |
| 20 | 11 | 5 | Human | 14 |
| 20 | 11 | 5 | Human | 14 |
| 20 | 11 | 5 | Human | 12 |
| 20 | 10 | 2 | Human | 6 |
| 20 | 9 | 3 | Human | 4 |
| 20 | 16 | 12 | Human | 2 |
| 20 | 15 | 14 | Human | 2 |
| 16 | 12 | 9 | Human | 2 |

As seen from the above table, the survival rate of the chimeric mice receiving the human liver graft was at the order of about 50–60%.

Figure 1B:
Figure 1C:
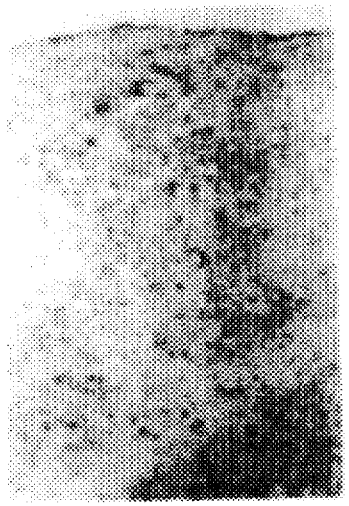
Figure 2A:
FIGS. 2A–2C show hepatocytes and bile duct-like structures (marked with arrows) in a transplanted human liver fragment 30 days after grafting at ×240 magnification (A); hepatocytes and epithelial cells at ×1200 magnification (B), bile duct-like structures at ×1200 magnification (C).
Figure 2B:
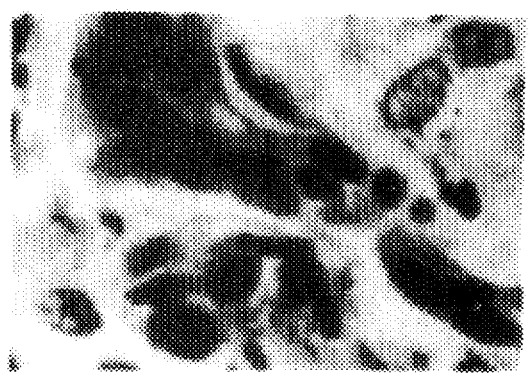
Figure 2C:
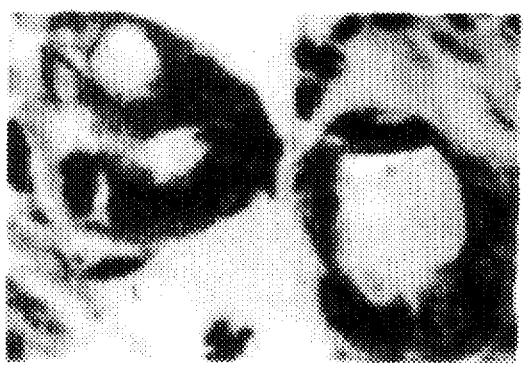

Histological examination of the transplanted liver fragments at this subcapsular area of the transplanted SCID→BNX chimera showed that following transplantation, the typical liver cell architecture disappeared and, in most transplants, central ischemia occurred while the peripheral tissue of the transplant was markedly fibrotic (see FIG. 1A–1C). In most cases, hepatocytes were recognized in addition to proliferating epithelial cells (FIG. 2A–2C) and the engrafted tissue mainly resembled the morphological characteristics of biliary epithelium (FIG. 2B and 2C). A very mild inflammatory reaction was occasionally observed consisting a few polymorphonuclear and plasma cells.

Evaluation of liver engraftment rate showed that among the mice receiving the human liver grafts, 15 out of 33 retained the graft for more than 12 weeks while 40 out of 62 were stably engrafted at six weeks or less (Table 1).

Example 2
Transplantation of Liver Tissue from a human infected with hepatitis B virus (HBV)

Figure 3A:
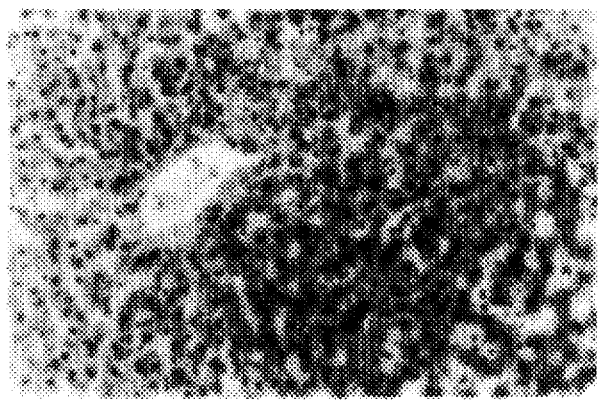
FIGS. 3A–3D show (A) histology of a liver segment prior to transplantation (H&E, ×100) (B), immunohistological staining for HBsAg of human liver, infected with HBV (×100) (C), periodic acid-Schiff staining for glycogen of a human liver (L) segment transplanted under the kidney (K) capsule of a SCID→BNX chimera (×50) and (D), immunohistological staining for HBsAg of human liver infected with HBV, as observed 19 days after transplantation at the subcapsular area of the SCID→BNX chimera kidney (×50). Staining was performed using, as a primary antibody, mouse anti-HBsAg (Zymed Lab, San Francisco, Calif.).
Figure 3B:
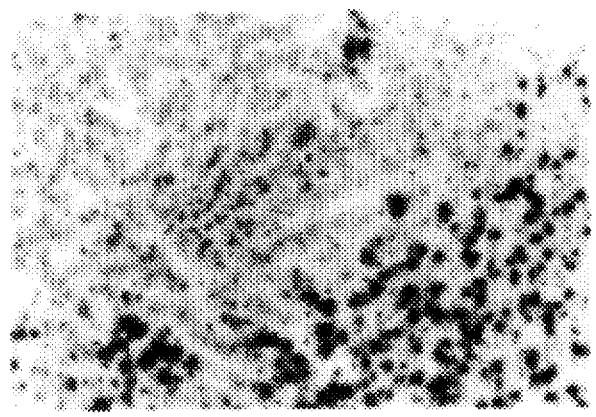
Figure 3C:
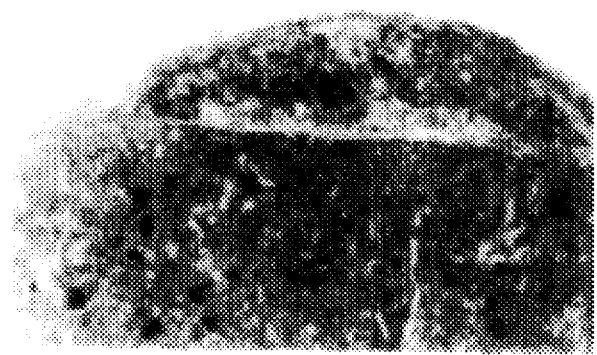
Figure 3D:
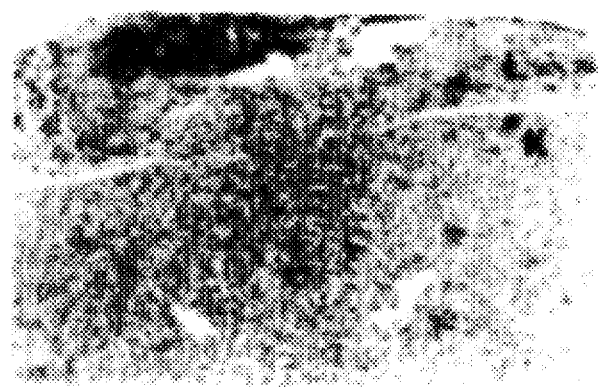

A liver biopsy from a patient infected with hepatitis B virus (HBV) was obtained and transplanted under the kidney capsule of SCID→BNX chimera mice as described in Example 1. Immmunohistology of the liver segment prior to transplantation showed that the hepatocytes stained positively for the HBV surface protein (HBsAg) (FIG. 3B). After transplantation, evidence was provided for the human origin of the transplanted cells by using staining with periodic acid-Schiff reaction which identifies glycogen in human hepatocytes (FIG. 3C). 19 days after transplantations the subcapsular area of the SCID→BNX chimera kidney was immunohistologically stained and HBsAg was detected in discrete areas of the cytoplasm in the engrafted tissue but not in the neighboring mouse kidney cells (FIG. 3D).

Example 3
Transplantation of Liver Fragments Infected in vitro with HBV

Liver fragments were obtained from non HBV infected humans as described in Example 1. The non infected human liver fragments were incubated in vitro with HBV resulting in their infection by HBV. The in vitro HBV infected liver fragments were transplanted under the kidney capsule of SCID→BNX mice as described in Example 1 and the detection of HBV in the transplanted mice was assessed either by immunohistology of the hepatocytes as described in Example 2 or by testing the level of HBV in the serum of the mice by PCR.

The results are shown in the following Table 2.

TABLE 2

Transplantation Results of in vitro Viral Hepatitis B Infected Human Livers in SCID→BNX Mice

| No. of Animals | No. of Animals, Survived | No. of Animals Engrafted | Route of Infection* | Infection Indicators and comments** |
|---|---|---|---|---|
| 10 | 5 | 5 | Pre-transplantation in vitro incubation of liver fragments with HBV-DNA, +ve sera | PCR +ve (3/5) |
| 10 | 7 | ND*** | Pre-transplantation in vitro incubation of liver fragments with HBV-DNA, +ve sera | PCR +ve 1/7 at day 11 PCR +ve 4/7 at day 30 |
| 10 | 5 | ND | Pre-transplantation in vitro incubation of liver fragments with HBV-DNA, +ve sera | PCR +ve 1/5 at day 11 |

*+ve sera = sera positive for viremia
**PCR +ve = PCR test positive for hepatitis virus DNA
***ND = No Data: Mice have not yet been sacrificed for histological examination.

As seen in the above table, HBV sequences were observed in the sera of some of the transplanted mice about ten days after transplantation and with progression of time after transplantation HBV sequences were observed in a larger number of transplanted mice.

Example 4
Detection of HCV in sera of mice transplanted with liver fragments from HCV infected patients Liver fragments from three patients with chronic HCV infection were obtained transplanted under the kidney capsule of SCID→BNX mice as described in Example 1. The presence and level of HCV in the serum of the transplanted mice was assessed by reverse transcriptase-nested-polymerase chain reaction (RT-PCR) as follows.

RNA was dissolved in 10 μl RNAase-free water. cDNA was synthesized using 50 ng of the antisense primer ASI in a reaction mixture containing 2×Taq polymerase buffer (Promega Corp., Madison, Wis.) 0.5 mM dNTP, 20 units RNAsin (Promega), 10 mM dithiothreitol and 30 units avian myeloblastosis virus reverse transcriptase (Life Sciences, Bethesda, Md.) for 60 min. at 42° C. PCR was performed in reaction mixture volume of 50 μl containing Taq Polymerase buffer (Promega), 2 mM dNTP, 1.5 mM $MgCl_2$, 20 ng of sense primer SI and 2.5 units Taq Polymerase (Promega). The reaction was carried out by 35 cycles of PCR consisting of 94° C. for 1.5 min. 55° C. for 1.5 min. and 72° C. for 3 min. The second PCR reaction was performed as before, with 5 μl of the first PCR reaction mixture and the nested set of primers SII (sense) and ASII (antisense). The two sets of primers used are from the highly conserved 5' untranslated region (5' UTR).

The following primers were used:

SI 7–26: 5'-CAC-TCC-ACC-ATA-GAT-CAT-CCC-3' (SEQ ID NO:1).

ASI 248–222: 5'-ACC-ACT-ACT-CGG-CTA-GCA-GT-3' (SEQ ID NO:2).

SII 46–65: 5'-TTC-ACG-CAG-AAA-GCG-TCT-AG-3' (SEQ ID NO:3).

ASII 190–171: 5'-GTT-GAT-CCA-AGA-AAG-GAC-CC-3' (SEQ ID NO:4).

The results obtained following transplantation of HCV infected liver fragments is shown in the following Table 3:

TABLE 3

Transplantation results of liver fragments from HCV infected human patients in SCID→BNX mice

| Transplanted with HCV infected liver fragments | Surviving | Stably Engrafted | Viremia positive |
|---|---|---|---|
| 20 | 17 | 15 | 8 |
| 17 | 14 | 10 | 7 |
| 13 | 11 | 6 | 5 |
| 12 | 10 | ND* | 6 |

*ND = No Data: mice have not yet been sacrificed for histological examination

Figure 4A:
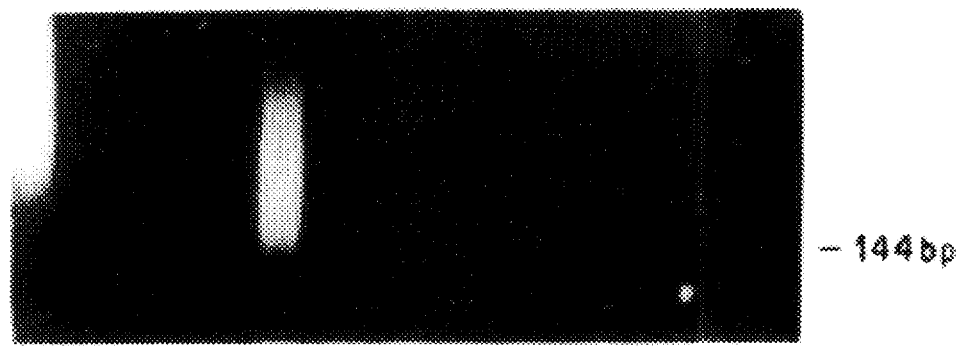
FIGS. 4A and 4B are electrophoretograms of cDNA of RNA samples extracted from sera of SCID→BNX chimera, transplanted under the kidney capsule with human liver infected with HCV, and subjected to RT-PCR amplification using two sets of primers as described in Example 4. Each lane represents a different mouse which was sacrificed at the day of sampling. The first 13 lanes, which are shown
Figure 4B:
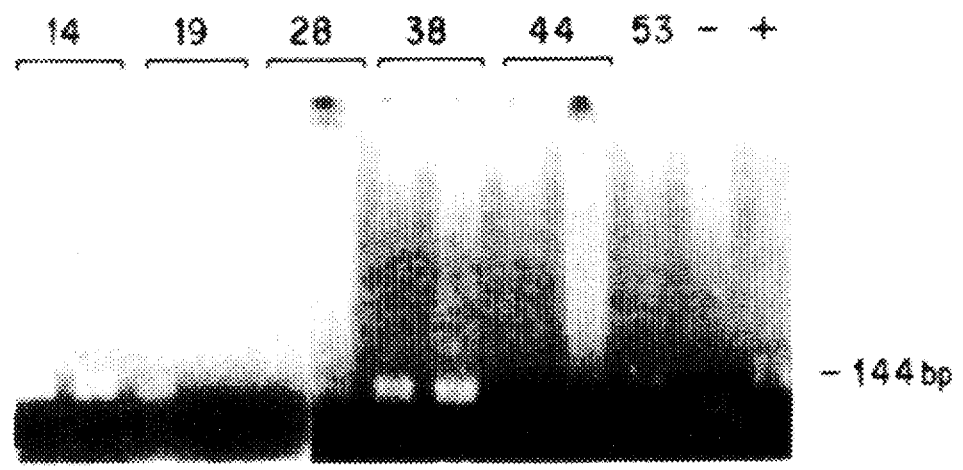

HCV sequences were first observed in the sera of the transplants mice two weeks post transplantation and contiiued to be detected intermittently for about two months after transplantation, at which time animals were sacrificed (a typical experiment is shown in FIG. 4A and 4B). Similar fluctuations in detection of the HCV RNA have been previously observed in chimpanzees experimentally infected with HCV and in chronically infected patients, probably resulting from the very low levels of the virus in the serum.

Example 5

Transplantation of Liver Fragments Infected in vitro with HCV to C3H Mice

C3H mice, which are not of an immune deficient strain, were irradiated by split total body irradiation (TBI) (a first dose of 400 rads and a second dose of 1,200 rads) and radioprotected the following day with $3\times10^6$ SCID bone marrow cells (as described in Example 1 above).

Liver fragments were obtained from non HCV infected humans as described in Example 1 and the non infected human liver fragments were incubated in vitro with HCV resulting in their infection by HCV. The in vitro HCV infected liver fragments were transplanted under the kidney capsule of the C3H mice as described above and the detection of HCV in the transplanted mice was assessed by testing the level of HCV in the serum of the mice by RT-PCR as described in Example 4 above.

The results are shown in the following Table 4:

TABLE 4

Transplantation Results of in vitro Viral Hepatitis C Infected Human Livers in C3H Mice

| No. of Animals | No. of Animals Survived | No. of Animals Engrafted | Route of Infection | Infection Indicators and comments*** |
|---|---|---|---|---|
| 10 | 10 | ND* | Pre-transplantation in vitro incubation of liver fragments with HCV-DNA, +HCV sera** | PCR +HCV 2/10 at day 14 |

*ND = No Data: Mice have no yet been sacrificed for histological examination
**+HCV sera = sera positive for HCV
***PCR +HCV = PCR test positive for hepatitis C virus DNA.

The results shown in the table above, demonstrate for the first time, that human liver fragments infected in vitro with HCV may be engrafted and result in the infection of the transplanted mice with HCV as assessed by the detection of HCV sequences in the sera of the transplanted mice.

In addition, the above results, for the first time, show that human HCV infected livers may be transplanted under the kidney capsules of C3H mice, which are not of an immune deficient strain.

I claim:

1. A chimeric mouse or rat having a stable transplant of xenogeneic liver tissue, useful as a model for human hepatitis virus (HV) infection, comprising a mouse or rat M5 having xenogeneic cells; said mouse or rat M5 being a mouse or rat M1, the hematopoietic cells of which have been substantially destroyed, and then transplanted with hematopoietic cells from one or more SCID mice M2 and transplanted with liver tissue from a xenogeneic mammal M3 of a species that can be infected by HV; said xenogeneic liver tissue in said mouse or rat M5 being infected by HV.

2. A chimeric mouse or rat according to claim 1, wherein the hematopoietic cells of said mouse or rat M1 are substantially destroyed by total body irradiation (TBI).

3. A chimeric mouse or rat according to claim 2, wherein the irradiation is a split total body irradiation (TBI).

4. A chimeric mouse or rat according to claim 1, 2 or 3, wherein said M3 mammal is an HBV or HCV infected mammal.

5. A chimeric mouse or rat according to claim 4, wherein the HBV or HCV infected mammal is a human hepatitis patient.

6. A chimeric mouse or rat according to claim 1, 2 or 3, wherein said M3 mammal is a non-HV infected mammal and the liver tissue is infected with HV in vitro prior to transplantation thereof into the M1 mammal.

7. A chimeric mouse or rat in accordance with claim 6, wherein said M3 mammal is a human.

8. A chimeric mouse or rat according to claim 1, 2 or 3, wherein said M3 mammal is a non-HV infected mammal, and the mammal obtained after transplantation (M4) is inoculated with HV.

9. A chimeric mouse or rat in accordance with claim 8, wherein said M3 mammal is a human.

10. A chimeric mouse or rat having a stable transplant of xenogineic liver tissue, useful as a model for the evaluation of the efficacy of anti-HV prophylactic treatment, comprising a mouse or rat M4, being a mouse or rat M1, the hematopoietic cells of which have been substantially destroyed, and then transplanted with hematopoietic cells from one or more SCID mice M2 and transplanted with non-HV infected adult liver tissue from a xenogeneic mammal M3 of a species capable of being infected by HV.

11. A chimeric mouse or rat according to claim 10, wherein the hematopoietic cells of said mouse or rat M1 are substantially destroyed by total body irradiation (TBI).

12. A chimeric mouse or rat according to claim 11, wherein the irradiation is a split total body irradiation (TBI).

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CACTCCACCA TAGATCATCC C        21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

ACCACTACTC GGCTAGCAGT        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TTCACGCAGA AAGCGTCTAG        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GTTGATCCAA GAAAGGACCC        20